(12) United States Patent
Lan et al.

(10) Patent No.: US 12,001,032 B2
(45) Date of Patent: Jun. 4, 2024

(54) GRATING STRUCTURE AND UV LIGHT

(71) Applicant: Shenzhen Guanke Technologies Co., Ltd, Shenzhen (CN)

(72) Inventors: Qing Lan, Shenzhen (CN); Shoubao Chen, Shenzhen (CN); Bo Lei, Shenzhen (CN); Jinliang Lei, Shenzhen (CN); Linjiang Wang, Shenzhen (CN)

(73) Assignee: Shenzhen Guanke Technologies Co., Ltd, Shenzhen (CN)

( * ) Notice: Subject to any disclaimer, the term of this patent is extended or adjusted under 35 U.S.C. 154(b) by 391 days.

(21) Appl. No.: 17/570,992

(22) Filed: Jan. 7, 2022

(65) Prior Publication Data

US 2023/0142466 A1   May 11, 2023

(30) Foreign Application Priority Data

Nov. 5, 2021   (CN) .......................... 202122705674.X

(51) Int. Cl.
 *G02B 5/00* (2006.01)
 *A61L 9/20* (2006.01)
 *G02B 5/20* (2006.01)

(52) U.S. Cl.
 CPC ................ *G02B 5/003* (2013.01); *A61L 9/20* (2013.01); *G02B 5/208* (2013.01); *A61L 2209/12* (2013.01); *A61L 2209/15* (2013.01)

(58) Field of Classification Search
 CPC .. G02B 5/003; G02B 5/208; G02B 2207/121; G02B 19/0047; G02B 19/0095; A61L 9/20; A61L 2209/12; A61L 2209/15
 See application file for complete search history.

(56) References Cited

FOREIGN PATENT DOCUMENTS

| CN | 203183369 U | * | 9/2013 |
| CN | 204446693 U | * | 7/2015 |
| CN | 111012940 A | * | 4/2020 |
| JP | 2017018442 A | * | 1/2017 |
| WO | WO-2014079135 A1 | * | 5/2014 |

* cited by examiner

*Primary Examiner* — David E Smith
*Assistant Examiner* — Christopher J Gassen
(74) *Attorney, Agent, or Firm* — Maier & Maier, PLLC

(57) ABSTRACT

A grating structure and a UV light, where the grating structure includes at least two up-down baffles provided at intervals, the upper surface and the lower surface of each baffle is provided with a light absorption layer, two adjacent baffles enclose to form a light outlet; in the light emission direction of the light outlet, each baffle includes the incoming light section, the light filter section and the outgoing light section, and the incoming light section, the light filter section and the outgoing light section are respectively the first plate body, second plate body and third plate body connected in sequence, the upper surface and the lower surface of the light filter section are provided respectively with multiple upper convexes and multiple lower convexes, the height difference of the top of the upper convexes and the bottom of the lower convexes is greater than 1.5 mm.

18 Claims, 14 Drawing Sheets

GRATING STRUCTURE AND UV LIGHT

TECHNICAL FIELD

The present invention relates to the technical field of lighting equipment, particularly to a grating structure and UV light that applies the grating structure.

BACKGROUND

The upper-layer flat irradiation UV light refers to the light that is installed into the upper space above 2.1 m (this height refers to the distance between the ground or the floor) and can horizontally emit UV rays (wavelength: 200-400 nm) to sterilize and disinfect the upper space. During sterilization of the upper-layer flat irradiation UV light, people do not need to leave the sterilization occasion, and can freely move or work in the lower space below 2.1 m, facilitating sterilization and disinfection.

In prior art, the upper-layer flat irradiation UV light will be provided with a grating structure on the outside of the UV light source, this grating structure usually contains many baffles provided horizontally and at intervals, and baffles are usually of a slab structure (including: all the baffles are in the slab shape (FIG. 1; or most baffles are in the slab shape, but there are a few of curve plates at the incoming light position (FIG. 2)), scattered UV rays from the UV light source can be emitted roughly in the horizontal direction after light interception via baffles (FIG. 1 and FIG. 2). To simplify expression, this grating structure is defined as the grating structure A, and all the "lights" below refer to "upper-layer flat irradiation UV light", unless otherwise specified.

As the mounting height of the upper-layer flat irradiation UV light is higher, it is safer in use. In prior art, lights (including lights of the grating structure A) have a relatively large luminous angle and low precision, so UV rays emitted by such lights are likely to reach the lower space below 1.2 m. Especially strong UV rays of the large-power UV light above 20 W bring greater safety hazards to the lower space. Thus, in prior art, to guarantee the service safety, lights are usually installed above 2.5 m, they are not suitable for being installed at a height of 2.1 m-2.5 m, even though this mounting height enables UV light to indirectly sterilize the lower space better. However, when lights in the prior art are installed at a height of 2.1-2.5 m, UV rays of such lights are also very likely to access the lower space below 2.1 m, the safety performance is poor, and usually such lights can only reach the low safety level in *IEC 62471 Photobiology Safety of Light and Light System*, i.e. risk group 1; it is hard to reach the safety level of exempt group.

Description: The luminous angle of the UV light in the present patent is a relative reference value which is different from the luminous angle of the white light source as defined. According to the standard of CIE, usually the luminous intensity of lighting fixtures is defined as 50% of the luminous intensity in the direction of the normal line, and the included angle between two lines is the luminous angle, i.e. half-intensity angle. The scheme of the present invention is the research on the safety of UV rays. Even though the UV ray radiation intensity in the lower space reaches 50% of that in the direction of the normal line, hazards may be brought to human body. So, the luminous angle in the present invention is the angle corresponding to safe radiation intensity.

SUMMARY

The main purpose of the present invention is to provide a grating structure applied to UV lights, aiming to make UV rays from UV lights be emitted horizontally after passing through the grating structure to lower the possibility of accessing the lower space and improve the service safety of UV lights.

To realize the above purpose, the grating structure in the present invention comprises at least two up-down baffles provided at intervals, the upper surface and the lower surface of each the baffle is provided with a light absorption layer, two adjacent baffles enclose to form a light outlet;

In the light emission direction of the light outlet, each the baffle comprises the incoming light section, the light filter section and the outgoing light section, and the incoming light section, the light filter section and the outgoing light section are respectively the first plate body, second plate body and third plate body connected in sequence, the upper surface and the lower surface of the light filter section are provided respectively with multiple upper convexes and multiple lower convexes, the height difference of the top of the upper convexes and the bottom of the lower convexes is greater than 1.5 mm.

BRIEF DESCRIPTION OF THE DRAWINGS

Many aspects of the embodiments can be better understood with reference to the following drawings. The components in the drawings are not necessarily dawns to scale, the emphasis instead being placed upon clearly illustrating the principles of the embodiments. Moreover, in the drawings, like reference numerals designate corresponding parts throughout the several views.

The shape, dimension, proportion or position relationship of parts of the product in drawings may be real data of embodiments and they are under protection of the present invention.

DETAILED DESCRIPTION

To make the objective, technical solutions and advantages of the present invention clearer and be understood better, further detailed descriptions of embodiments of the present invention are made in combination with drawings. Understandably, the specific embodiments described are just used to explain but not limit the present invention.

The solving ideas of technical problems of the present invention and relevant product design solutions are as shown below:

I. Standard Analysis:

According to the IEC 62471 Photobiology Safety of Light and Light System, to make UVC UV sterilization light reach the safety level of risk group 1 (RG1), the radiation value of photochemical UV rays (ES) whose wavelength is 200-400 nm needs to be reduced to be lower than 0.003 W/m$^2$; to realize the safety level of exempt group (RG0), the radiation value of photochemical UV rays (ES) whose wavelength is 200-400 nm needs to be reduced to be lower than 0.001 W/m$^2$.

Figure 1:
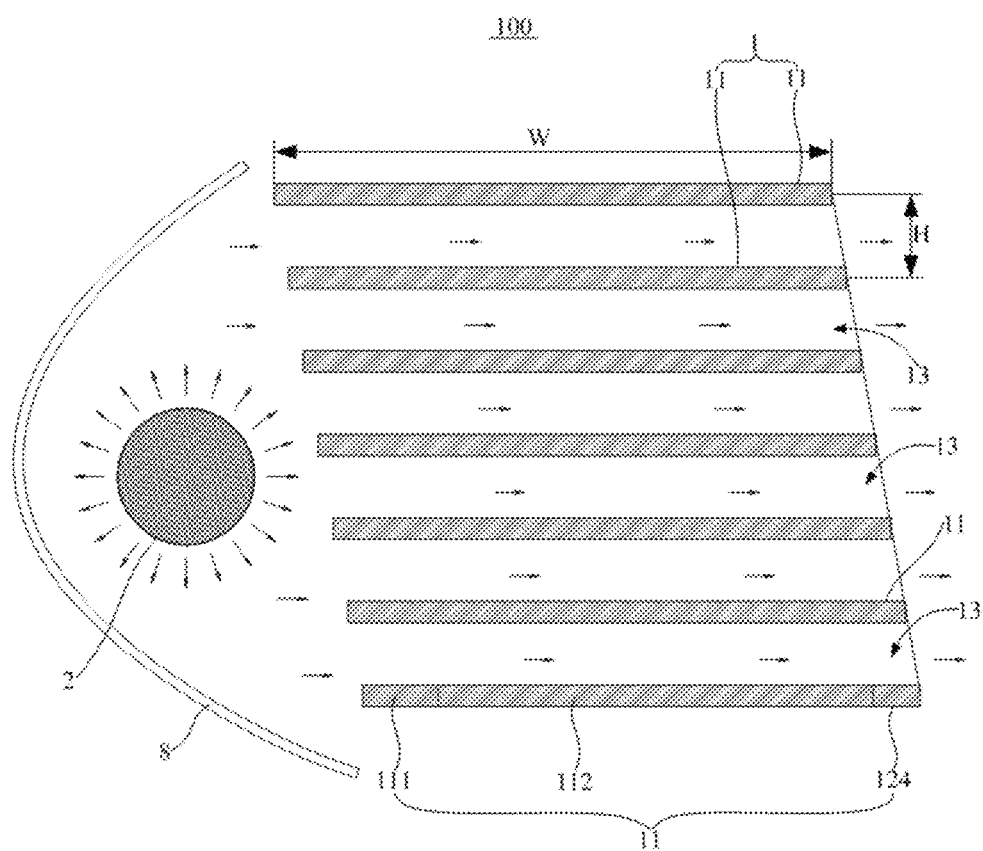
FIG. 1 is a schematic diagram showing the cross section of the UV light in one embodiment of horizontal grating scheme A in the outgoing light direction.
Figure 2:
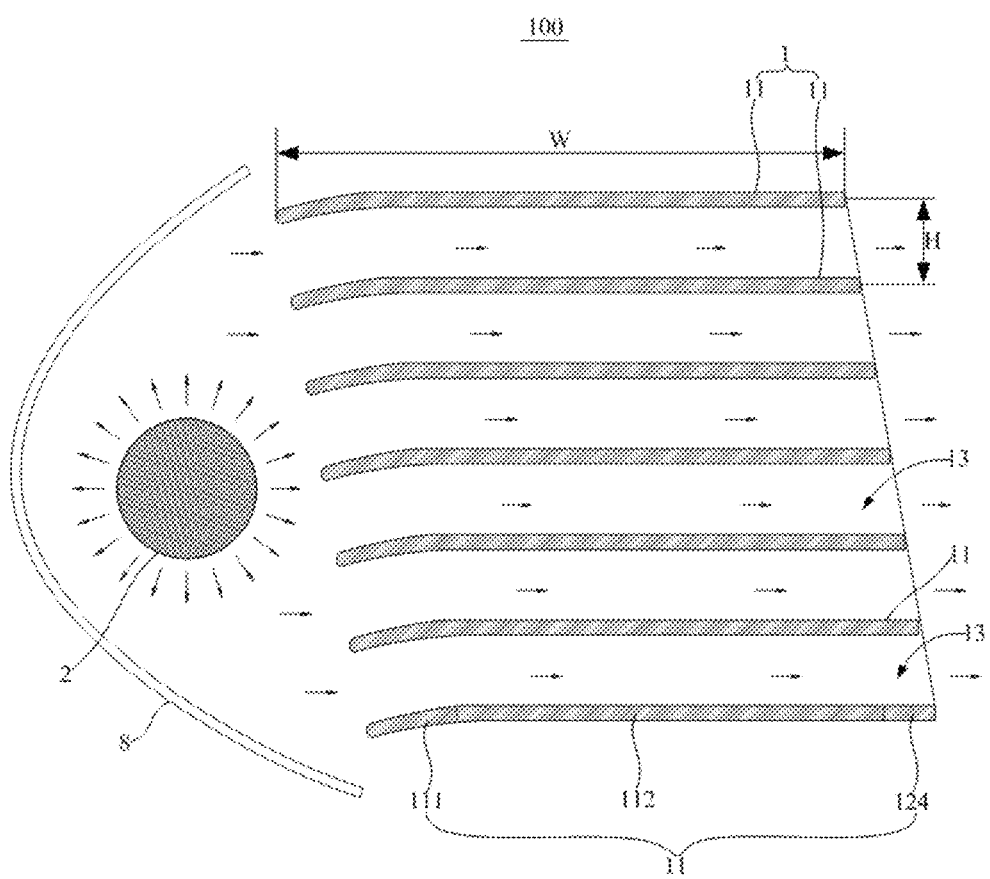
FIG. 2 is a schematic diagram showing the cross section of the UV light in another embodiment of horizontal grating scheme A in the outgoing light direction.

II. Introduction to Characteristics of the Horizontal Grating Scheme A:

In scheme A (FIG. 1 and FIG. 2), the grating structure 1 contains multiple baffles 11 provided horizontally and at intervals (FIG.s only present 7 baffles 11, all such baffles can be of a slab structure; or most baffles 11 are of a slab structure, but there is a few of curve plates at the incoming light section), and the clearance between adjacent baffles 11 constitutes the light outlet 13. Each baffle 11 comprises the incoming light section 111, light filter section 112 and outgoing light section 124 connected in sequence in the width direction, and the incoming light section 111, light filter section 112 and outgoing light section 124 are basically on the same plane. The surface of the baffle 11 is provided with a light absorption layer that can absorb UV rays. When UV rays from the UV light source 2 on one side of multiple baffles 11 are emitted outside the light body via the light outlet 13, partial UV rays at the incoming light section 111 will be intercepted, partial UV rays can be emitted via the light outlet 13 or after refraction on the surface of baffles 11, partial UV rays emitted via the light outlet 13 are absorbed by the surface of baffles 11, or can be refracted and absorbed after their intensity is weakened, so that UV rays can be emitted roughly in the horizontal direction via the grating subassembly. However, in scheme A, the grating structure 1 has a relatively large luminous angle and low precision, so UV rays emitted by such lights are likely to reach the lower space below 1.2 m. Especially strong UV rays of the large and medium-power UV light above 20 W bring greater safety hazards to the lower space. In other words, lights usually can only reach the low safety level in IEC 62471 Photobiology Safety of Light and Light System, i.e. risk group 1; it is hard to reach the safety level of exempt group.

Figure 3:
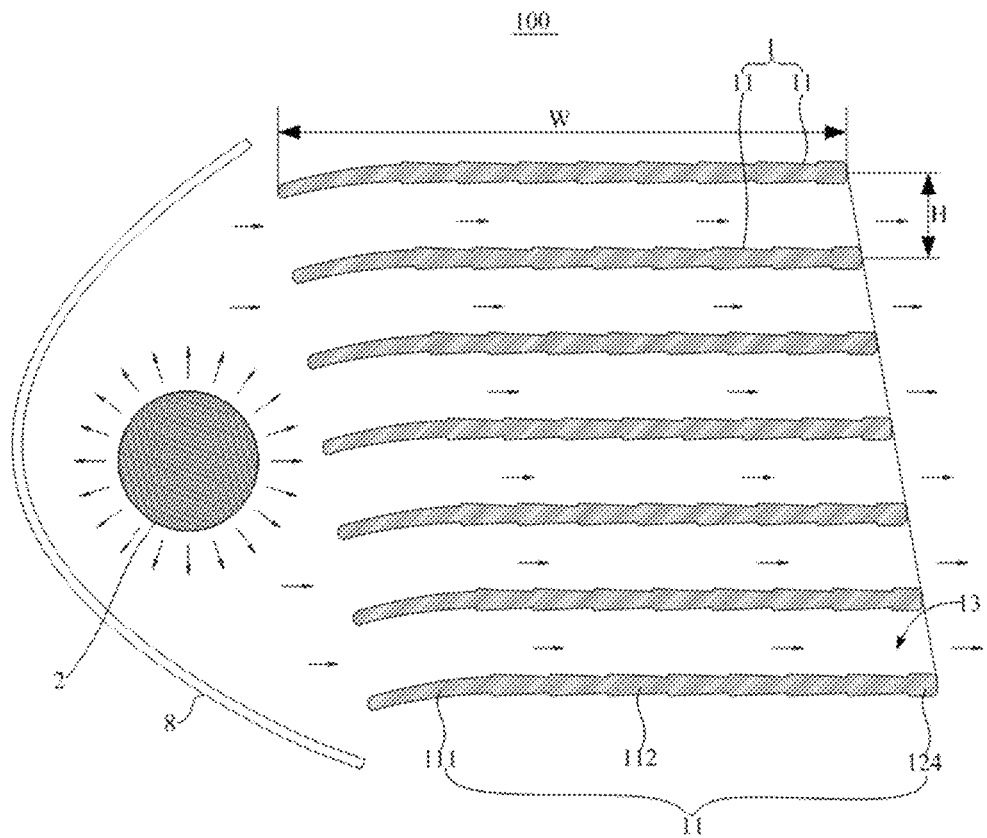
FIG. 3 is a schematic diagram showing the cross section of the UV light in the outgoing light direction in stepwise grating scheme B.
Figure 4:
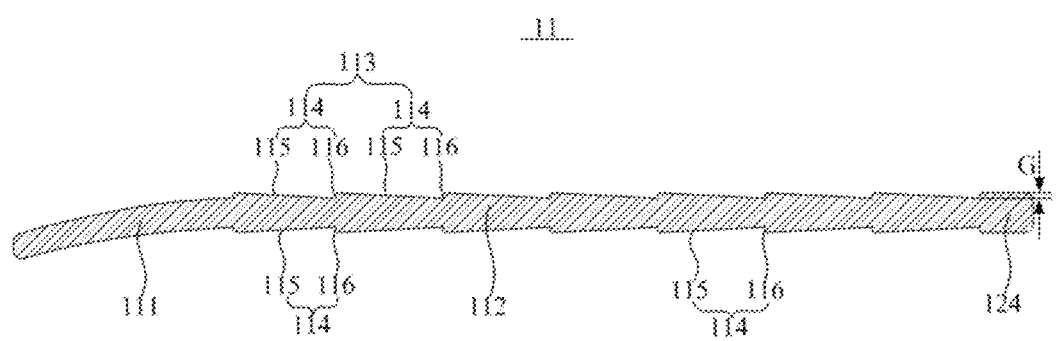
FIG. 4 is a schematic diagram showing the cross section of baffles in FIG. 3.

III. Introduction to Characteristics of the Stepwise Grating Scheme B:

Scheme B is another technical scheme that is the result of improvement of the scheme A, by keeping the width W and the clearance H of baffles 11 unchanged. In the scheme B (FIG. 3 and FIG. 4), the incoming light section 111 is bent downward, enabling it to better intercept upward or downward UV rays. Excessively downward or upward UV rays are inconsistent with the horizontal outgoing light direction, and it is hard to calibrate the emission direction of UV rays via baffles 11, so UV rays cannot be emitted via the light outlet 13. Thus, it is understood that interception of this part of UV rays at the incoming light section 111 is the first layer of filter of UV rays. In other embodiments, the incoming light section 111 can also be provided to be bent upward. Further, to improve the UV ray filter function of light filter section 112, the light filter section 112 of baffles 11 on the upper side and the lower side can form stepwise patterns 113 that include multiple steps 114 provided in sequence in the outgoing light direction of the light outlet 13, each step 114 comprises a long side 115 and a short side 116, the short side 116 is provided by facing the incoming light section 111 (the height G of the short side 116 of this step 114 can be about 0.2-0.5 mm). Thus, when UV rays that have a great angle with the horizontal direction irradiate onto the short side 116 of step 114, the short side 116 of the step 114 can reflect such UV rays to realize filter of non-horizontal UV rays by the light filter section 112. Also, the surface of the light filter section 112 is provided with stepwise patterns 113, and the area of the surface of baffles 11 can be increased to improve the UV ray absorption capacity of the surface of baffles 11. Further, the long side 115 can be provided upward in an inclined way by facing the incoming light section 111, so that it can collaborate with the short side 116 and receive partial UV rays reflected by the short side 116 and reflect again such UV rays. After several times of reflection, such UV rays are absorbed by the light absorption layer on the baffles 11 gradually. And, the short side 116 can be a straight vertical side or curve side, or the bottom of the short side 116 can be a straight side, while its top and the long side 115 on adjacent steps 114 are provided in the arc transition form.

Additionally, like scheme A, the UV light source 2 in scheme B is 30 W, the grating structure 1 comprises 7 baffles 11, the width W of baffles 11 is 57 mm, and the clearance of baffles 11 is 8.6 mm. During testing of the UV light 100, the mounting height of its bottom (regarded as the bottom of grating structure 1) is 2.3 m from the ground. In such a case, the UV ray radiation intensity scope on the horizontal plane at the height of 2.1 m in testing is: 0.001-0.003 W/m$^2$, and the UV light 100 belongs to the risk group 1.

Figure 5:
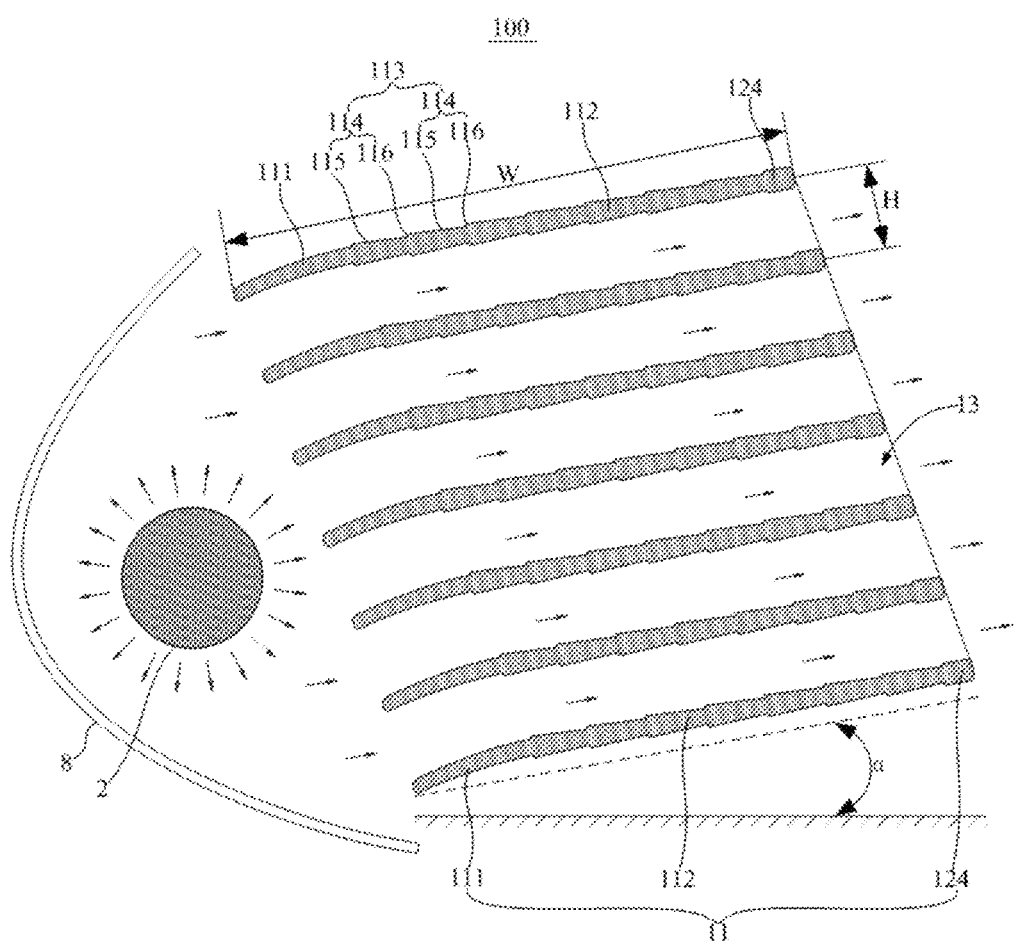
FIG. 5 is a schematic diagram showing the cross section of the UV light in the outgoing light direction in inclined angle scheme C.

IV. Introduction to characteristics of the inclined angle scheme C:

Scheme C as the further improvement of scheme B is shown in FIG. 5. On the basis of the grating structure 1 in scheme B, the grating structure 1 is inclined to make the incoming light section 111 of baffles 11 inclined upward by facing the outgoing light section 124, that is, there is an included angle (defined as a) between baffles 11 and the horizontal plane to from the grating structure 1 in scheme C. During the test, the radiation intensity of UV rays at the height of 2.1 m is tested once for increase of each 1° of the included angle from 0°. According to the test data, when the included angle (i.e. the "angle of inclination") reaches above 10°, the radiation intensity of UV rays at the height of 2.1 m will reduce to 0.001 W/m² and reach the safety level of exempt group. Thus, by providing the grating structure 1 to be inclined upward in scheme C, the UV light 100 can reach the safety level of exempt group, but when the angle of inclination of grating structure 1 reaches 10°, the effective radiation distance of 30 W UV light source 2 can reach 5 m, and the difference of inclination height of UV rays will be more than 0.868 m (=5 m)*sin 10°. The best sterilization scheme of the patented product aims to realize more UV rays within the height difference of 0.4 m at the height of 2.1-2.5 m without access to the lower space. For UV rays whose effective radiation distance can reach 5 m, if inclination of UV rays needs to be within the height difference of 0.4 m, the corresponding ideal angle of inclination should be smaller than 4.59° [=arcsin (0.4 m/5 m)]. In such a case, the safety angle of inclination 10° of scheme C is far greater than 4.59°. So, the angle of inclination of the grating structure 1 of the scheme C is too big, UV rays is further from the lower space, and cannot realize indirect sterilization of the lower space very well. Nevertheless, the indirect sterilization effect of the scheme C in the lower space is still better than that of the scheme A and scheme B, because scheme C can not only guarantee that the radiation intensity of UV rays in the lower space is lower than 0.001 W/m² as required in the standard and can also guarantee that many UV rays access the space at the height of 2.1-2.5 m.

V. Introduction to Characteristics of the Waveform Grating Scheme D:

Scheme D is the further improvement of scheme A, scheme B and scheme C. Specifically speaking, in scheme D (FIG. 6), it is defined as that the UV light 100 possesses an up-down direction, the grating structure 1 comprises at least two baffles 11 provided at intervals in the up-down direction, the upper surface and the lower surface of each baffle 11 are provided with a light absorption layer, and two adjacent baffles 11 enclose each other to form a light outlet 13; In the outgoing light direction of light outlet 13, each baffle 11 comprises the incoming light section 111, light filter section 112 and outgoing light section 124, and the incoming light section 111, light filter section 112 and outgoing light section 124 respectively connect to the first plate body 125, the second plate body 126 and the third plate body 127 in sequence, the upper surface and the lower surface of the light filter section 112 are respectively provided with multiple upper convexes 117 and multiple lower convexes 118, and the height difference of the top of the upper convexes 117 and the bottom of the lower convexes 118 is greater than 1.5 mm.

Figure 7:
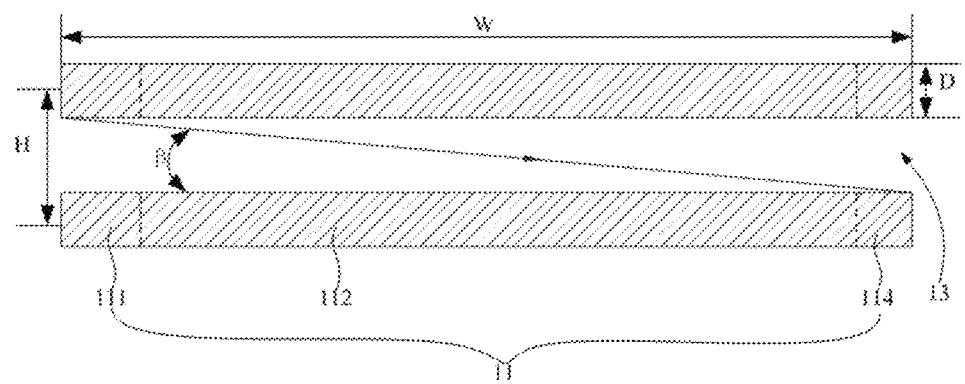
FIG. 7 is a schematic diagram showing the cross section of the grating structure.

For different grating schemes (FIG. 7), provided that the width of the baffle 11 is W, the thickness of the baffle 11 is D, and the clearance of adjacent baffles 11 is H, light outlet 13 possesses a critical angle β, when the included angle between the edge of UV rays and the horizontal angle is greater than β, UV rays cannot directly pass through the light outlet 13, and the trigonometric function of the critical angle is tan β=(H−D)/W.

In this scheme D, the incoming light section 111 of the grating structure 1 restrict UV rays whose included angle with the horizontal angle is greater than the critical angle β to be emitted into the light outlet 13 to intercept partial UV rays that are hard to pass through the light outlet 13 in advance.

Further, UV rays whose included angle with the horizontal plane is smaller than the critical angle β are restricted by upper convexes 117 and lower convexes 118 at the light filter section 112, after entering the light filter section 112, and then UV rays in the horizontal direction and UV rays approaching the horizontal direction can pass through the light outlet 13 smoothly; while other UV rays whose included angle with the horizontal plane is big will be gradually absorbed or attenuated between upper convexes 117 or lower convexes 118, and then will be emitted via the outgoing light section 124. As a result, it can be realized that the luminous angle of the grating structure 1 can be reduced without increasing the width of the baffle 11 or narrowing the clearance of the baffle 11. With the same testing condition of the scheme A, scheme B and scheme C, it is found that even the baffle 11 in scheme D is provided horizontally, when the UV light 100 is provided at a height of 2.1-2.5 m (this height refers to the distance from the ground or the floor), the radiation intensity of UV rays in the lower space can reach the safety level of exempt group; this also enables the UV light 100 to emit more UV rays into the space of 2.1-2.5 m, which will improve the direct sterilization capacity in the low-height area in the upper space, make air in the upper space exchange with the air in the lower space better and improve its indirect sterilization capacity in the lower space.

Further, the scheme D in one embodiment is defined as scheme D1. In scheme D1 (FIG. 6 and FIG. 8), the second plate body 126 is provided in a curve shape to form multiple upper convexes 117 and multiple lower convexes 118, at least partial upper convexes 117 and lower convexes 118 connect in sequence to form a continuous waveform structure, adjacent upper convexes 117 and lower convexes 118 of the continuous waveform structure are connected by the first section 119.

Figure 8:
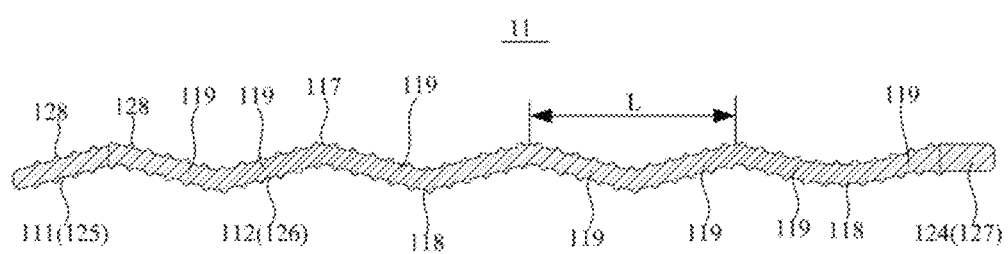
FIG. 8 is a schematic diagram showing the cross section of baffles in FIG. 6.
Figure 9:
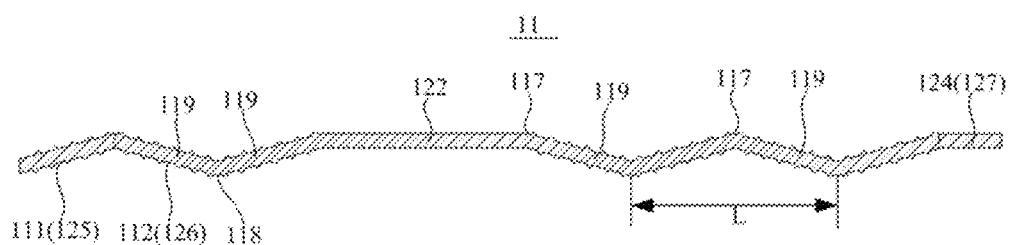
FIG. 9 is a schematic diagram showing the cross section of baffles in the waveform grating scheme D2.
Figure 10:
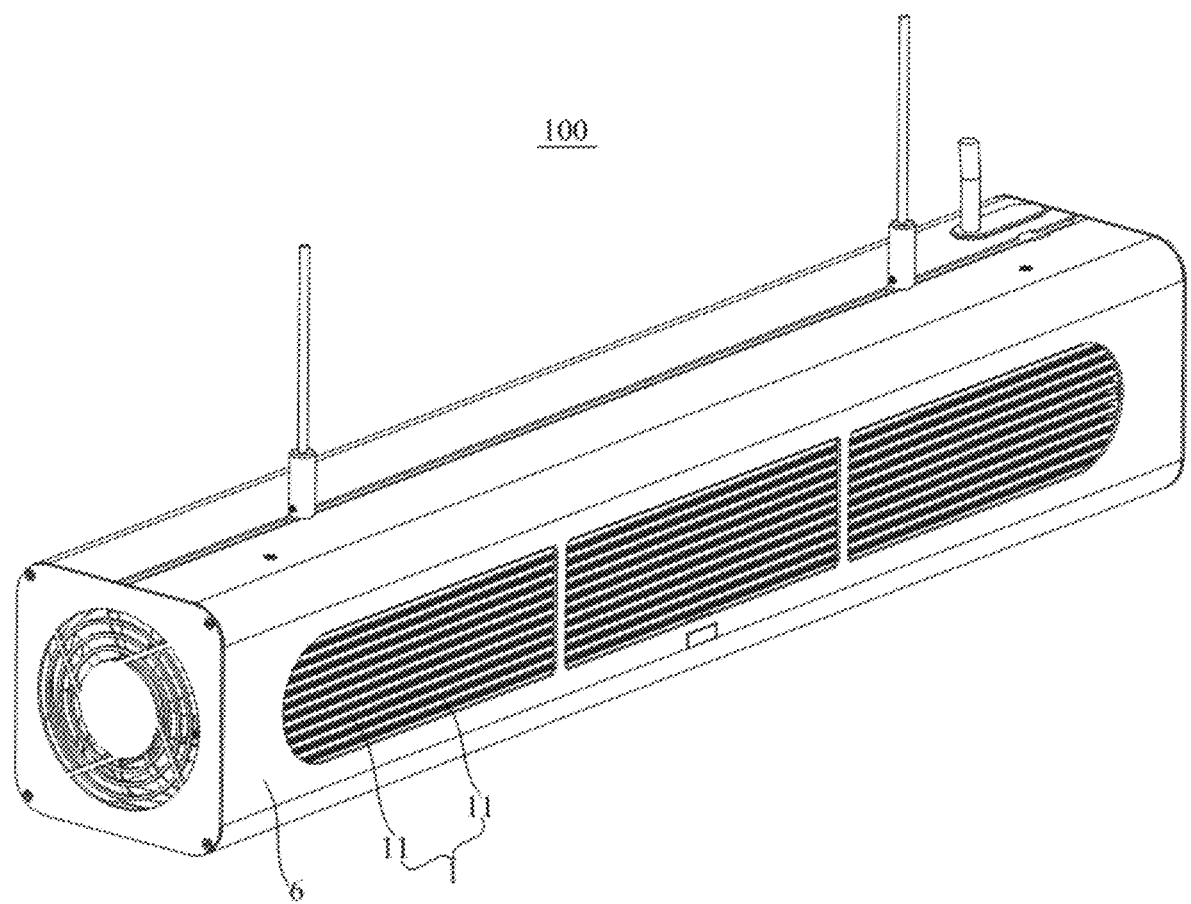
FIG. 10 is a schematic diagram showing the structure of the UV light in waveform grating scheme D2.
Figure 11:
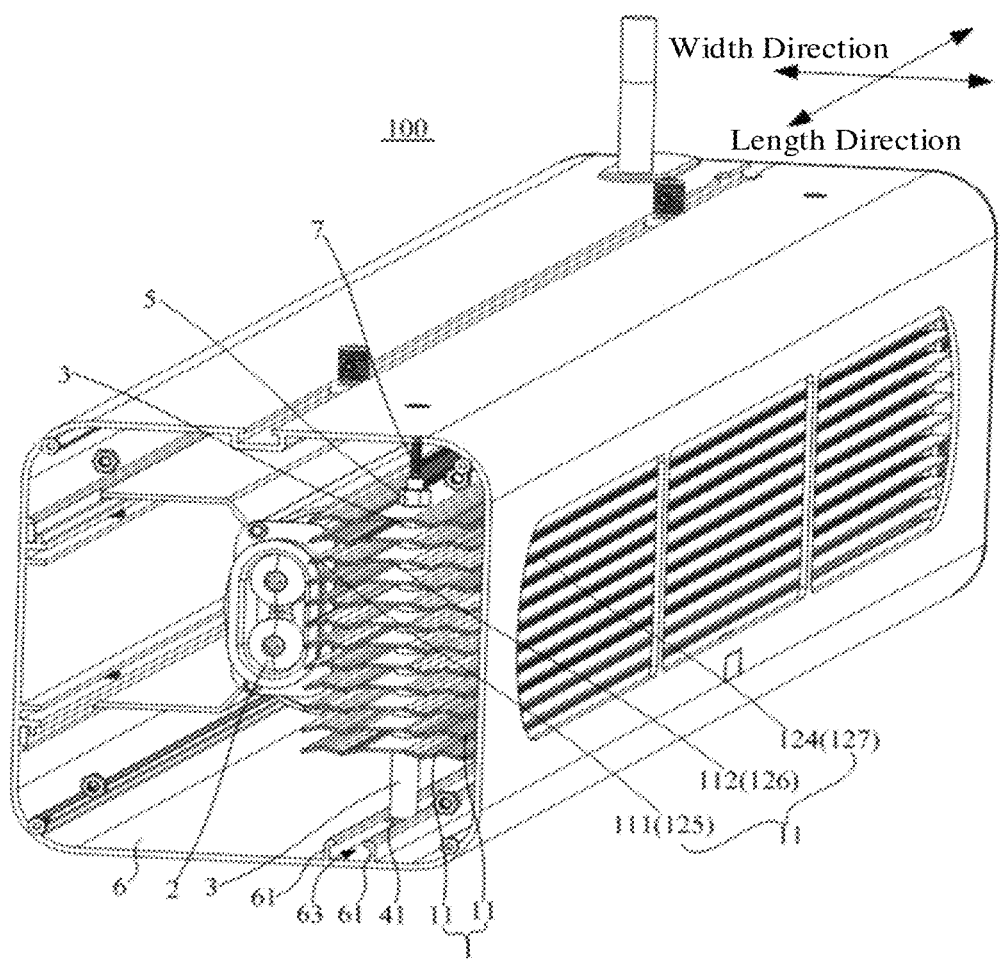
FIG. 11 is a schematic diagram showing the local structure of the UV light in FIG. 10.
Figure 12:
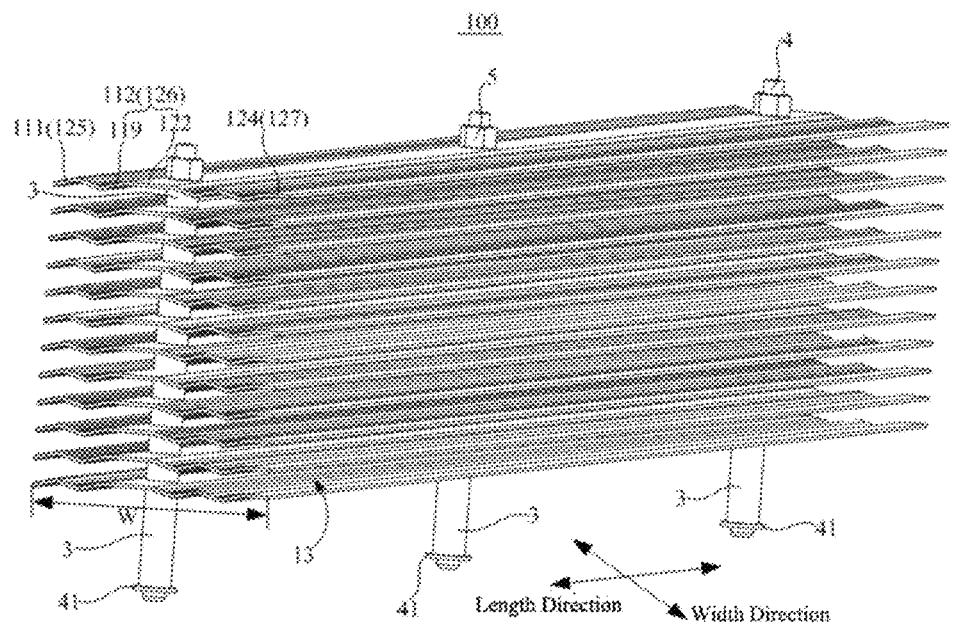
FIG. 12 is a schematic diagram showing the another local structure of the UV light in FIG. 10.
Figure 13:
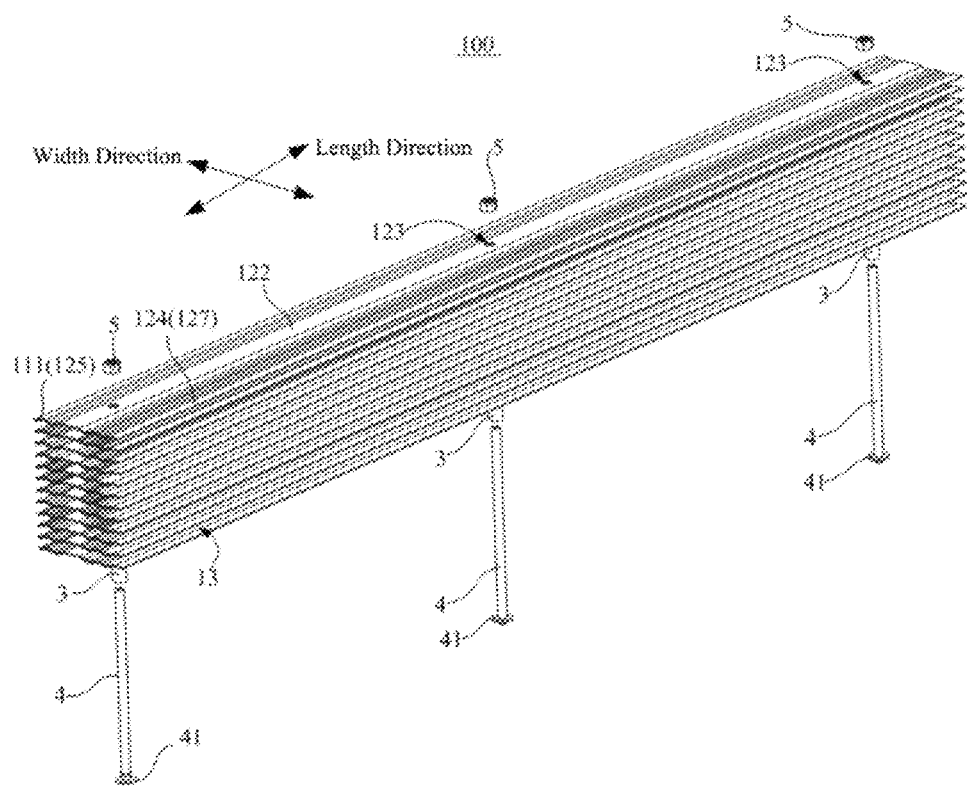
FIG. 13 is a schematic diagram showing the explosion structure of local structure of the UV light in FIG. 12.

In this embodiment, the curve second plate body 126 directly forms the upper convexes 117 and the lower convexes 118, enabling the upper convexes 117 and the lower convexes 118 to be processed easily, without adding an additional structure on the second plate body 126. Wherein, the second plate body 126 is in the curve shape. It can be bent on the plane or on a curve surface. However, the waveform structure can be continuous (FIG. 8); or it can be incontinuous (FIG. 9). In addition, as shown in FIG. 8, the upper surface and the lower surface of multiple first sections 119 can be plane; or the upper surface and the lower surface of the first section 119 can be curve; or, the upper surface and the lower surface of partial first sections 119 are plane, and the upper surface and the lower surface of other first sections 119 are curve. Wherein, the clearance L between adjacent upper convexes 117 or adjacent lower convexes 118 can be 12 mm.

In another embodiment of the scheme D, it is defined as scheme D2. In scheme D2 (FIG. 9), when the second plate body 126 is provided in a curve shape to form multiple upper convexes 117 and multiple lower convexes 118, and at least partial upper convexes 117 and lower convexes 118 connect in sequence to form a continuous waveform structure; the light filter section 112 comprises two continuous waveform structures connected via the second section 122, the second section 122 is a horizontal plate body structure, while both ends of the second section 122 can respectively connect two adjacent first sections 119.

In this embodiment, the second section 122 is of a horizontal plate body structure, its shape is relatively regular to form a mounting surface, facilitating installation via the relatively regular second section 122. Specifically speaking, in the UV light 100 comprising the grating structure 1 in the scheme D2 (FIG. 10-FIG. 13), the UV light 100 also comprises multiple connecting cylinders 3 whose ends are connected, the central columns 4 and nut 5; one end of one of multiple connecting cylinders 3 is against the lower surface of the lowest baffle 11, opposite two ends of other connecting cylinders 3 are against the part between two adjacent baffles, and the position of multiple baffles 11 corresponding to the connecting cylinders 3 is provided with mounting holes 123; the central columns 4 pass through multiple connecting cylinders 3 and mounting holes 123, the lateral peripheral surface of the lower end of the central columns 4 is provided with a convex mounting part 41 against the lower surface of the lowest connecting cylinder 3; threads of the nut 5 connect to the upper end of the central columns 4 and are against the upper surface of the top baffle 11, the nut 5 collaborates with the central columns 4 to clamp and fix multiple baffles 11 and multiple connecting cylinders 3. In such a case, multiple baffles 11 can be connected with at least two central columns 4 to improve the connection stability of multiple baffles 11 in the scheme D2. Further, to improve the stability of installation of the grating structure 1 to the UV light 100 in scheme D2, the UV light 100 also comprises a housing 6 and crews 7; the inner bottom wall of the housing 6 connects to two bending plates 61 that are opposite and provided at intervals and enclose with the inner bottom wall of the housing 6 to form the chute 63; the grating structure 1 is provided inside the housing 6, the convex mounting part 41 on the lower end of the central column 4 is installed inside the chute via two bending plates 61, the upper surface of the convex mounting part 41 is against the top wall of the chute 63; screws 7 pass through the top wall of the housing 6 and insert into the top pend of central column 4 and connect to the central column 4 through threads to make the grating structure 1 fix into the housing 6. In such a case, the lower end of the central column 4 slides from one end of two bending plates 61 into the chute 63 to make the convex mounting part 41 of the central column 4 against the top wall of the chute 63 to locate the convex mounting part 41. In the meanwhile, the grating structure 1 can be mounted and fixed quickly by connecting the screws 7 on the top wall of the housing 6 to the upper end of the central column 4. Wherein, the convex mounting part 41 can be a convex ring forming an integrated structure with the central column 4, or can be a gasket fixed onto the central column 4 via screws, and both bending plates 61 can be of a L-shaped structure. The nut 5 and the screw 7 can be other fastening or locating structures.

Figure 14:
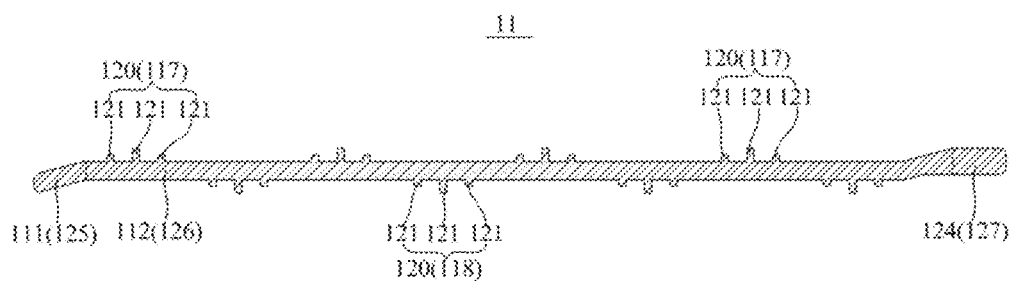
FIG. 14 is a schematic diagram showing the cross section of baffles in the waveform grating scheme D3.

Further, the scheme D in one embodiment is defined as scheme D3. In the scheme D3 (FIG. 14), the second plate body 126 is provided in the slab shape, the light filter section 112 comprises multiple convex rib groups 120, partial convex rib groups 120 are provided on the upper surface of the second plate body 126 to form multiple upper convexes 117, partial convex rib groups 120 are provided on the lower surface of the second plate body 126 to form multiple lower convexes 118.

In this embodiment, the second plate body 126 is roughly of a slab structure which is relatively simple and easy to process. Wherein, one convex rib group 120 forms an upper convex 117 or lower convex and comprises one convex rib 121. Of course, there can be multiple convex ribs 121 and the height of multiple convex ribs 121 can be different (for example, the middle multiple convex ribs 121 can be high, and those on both ends are low).

Figure 15:
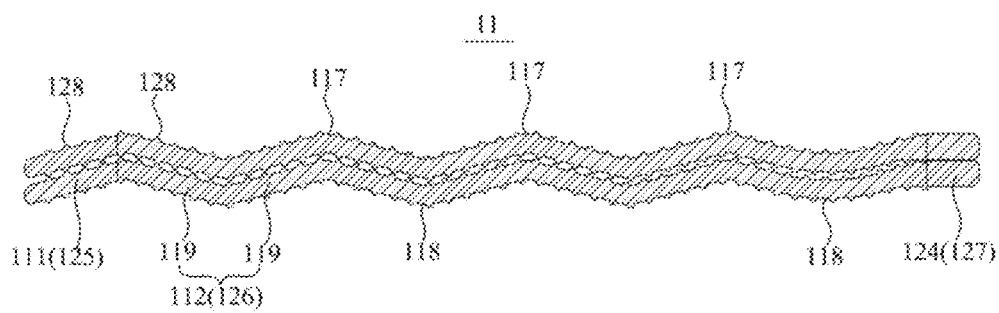
FIG. 15 is a schematic diagram showing the stacking structure of baffles in waveform grating scheme D1.
Figure 16:
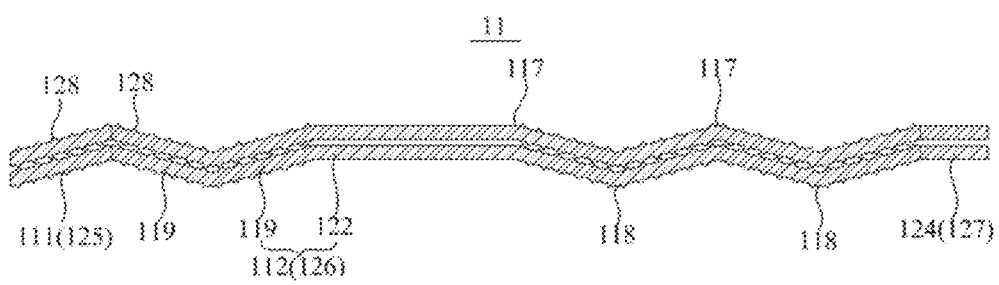
FIG. 16 is a schematic diagram showing the stacking structure of baffles in waveform grating scheme D2.
Figure 17:
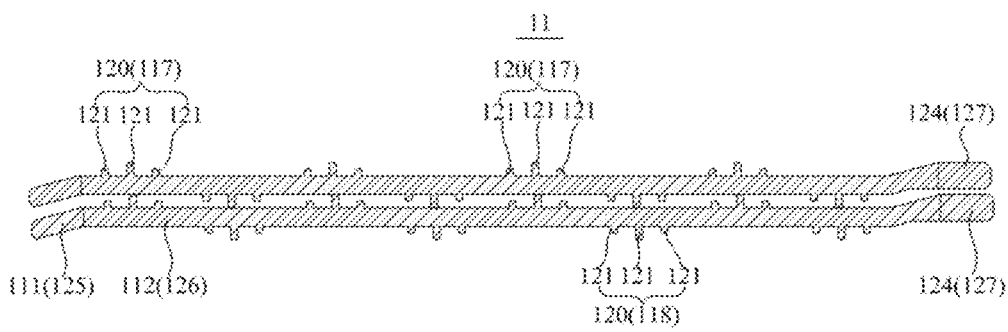
FIG. 17 is a schematic diagram showing the stacking structure of baffles in waveform grating scheme D3.

Further, some common characteristics in scheme D1, scheme D2 and scheme D3 can be provided as follows:

As shown in FIG. 15-FIG. 17, in one embodiment, the upper surface of the baffle 11 constitutes the upper outline, the lower surface of the baffle 11 constitutes the lower outline, when multiple baffles 11 are stacked, the upper outline can be against the lower outline.

When multiple baffles 11 are stacked, their load bearing can be more even, reducing the possibility that the surface of baffles 11 is scratched, better protecting the light absorption layer on the surface of the baffle 11. At the same time, such setting can reduce the stacking volume and facilitate transportation and storage. In addition, the lamination of the upper outline and the lower outline can prevent baffles 11 sliding down during stacking, which will improve the placement stability.

As shown in FIG. 15, in one embodiment, the upper surface and the lower surface of baffles 11 are provided with multiple convex patterns 128 or concave patterns vertical to the outgoing light direction. Different from the upper convexes 117 and the lower convexes 118, convex patterns 128 or concave patterns are designed to increase the surface area of baffles 11 to improve the UV ray absorption capacity of baffles 11. The diameter or width of the convex patterns 128 or concave patterns is usually smaller than 0.5 mm; while the height difference of the upper convexes 117 and the lower convexes 118 is usually greater than 1.5 mm, and the clearance of adjacent upper convexes 117 or adjacent lower convexes 118 is usually greater than 5 mm. Wherein, the first section 119 of the baffle 11 can be provided with convex patterns 128 or concave patterns. Further, when the baffle 11 is provided with the first section 119, the convex patterns 128 or concave patterns can be provided on the upper surface and the lower surface of each first section 119. When the second plate body 126 of the baffle 11 is provided with multiple convex rib groups 120, the convex patterns 128 or concave patterns can be provided on the upper surface and the lower surface of the area of the second plate body 126 that is not provided with convex rib groups 120.

In one embodiment, the baffle 11 is made of aluminum alloy that is easy to form and process; the surface of baffle 11 is processed with black anodic oxidation, and the light absorption layer is formed through oxidation treatment of the baffle 11.

Such design can improve the UV ray absorption efficiency of baffle 11, and then improve the UV ray filter effect.

In one embodiment (FIG. 15), the incoming light section 111 is bent upward or downward.

Since upward or downward outgoing UV rays whose included angle with the horizontal angle is greater than the critical angle β is inconsistent with the horizontal outgoing light, their emission direction is hard to be calibrated via the baffle 11. Such UV rays can be reflected well via upward bent incoming light section 111, so that upward or downward UV rays at the incoming light section 111 can be intercepted well. Similarly, the incoming light section 111 can be bent downward too.

In one embodiment, the outgoing light section 124 is provided in the form of horizontal extension.

In such a case, the horizontal setting of the outgoing light section 124 can better guide the outgoing light direction of the grating structure 1 to form the basically horizontal UV rays.

Figure 18:
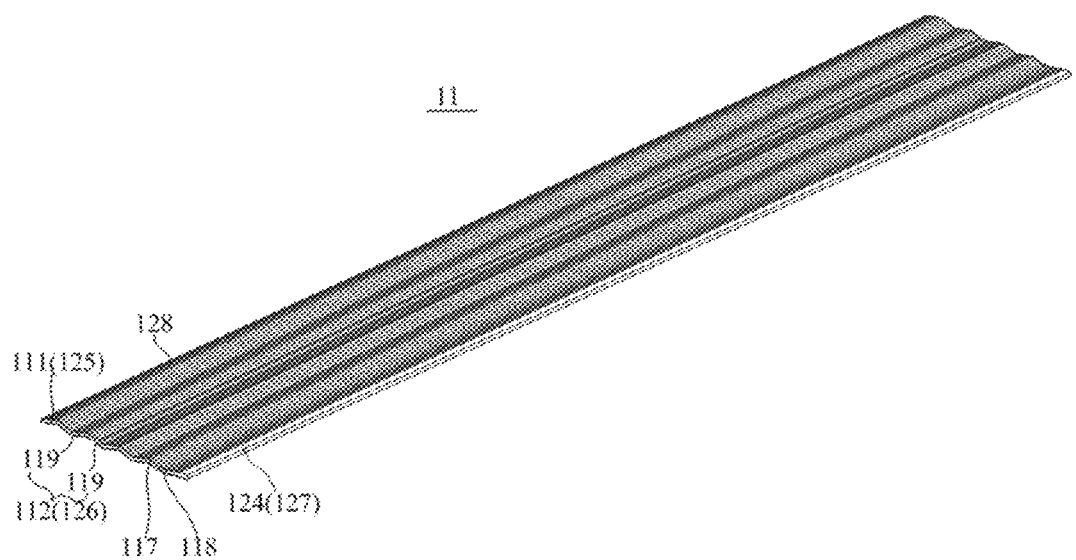
FIG. 18 is a schematic diagram showing the structure of baffles of the waveform grating scheme D1 in one embodiment.
Figure 19:
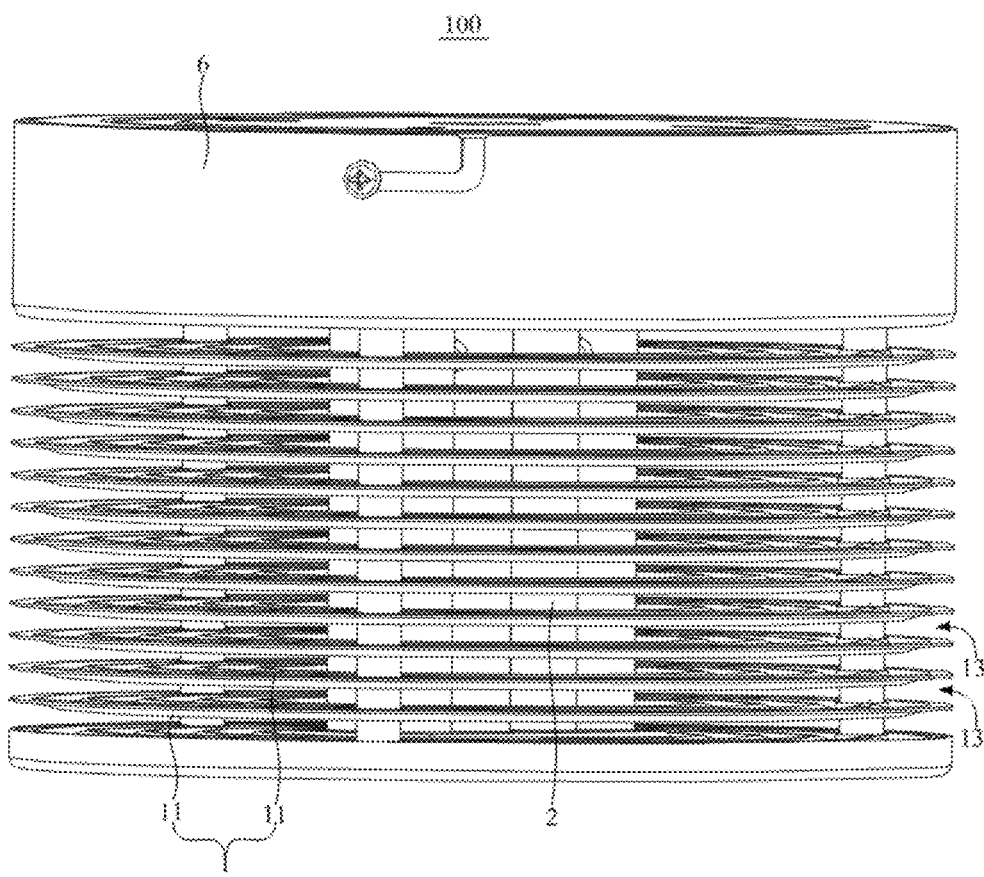
FIG. 19 is a schematic diagram showing the structure of the UV light in waveform grating scheme D in another embodiment.
Figure 20:
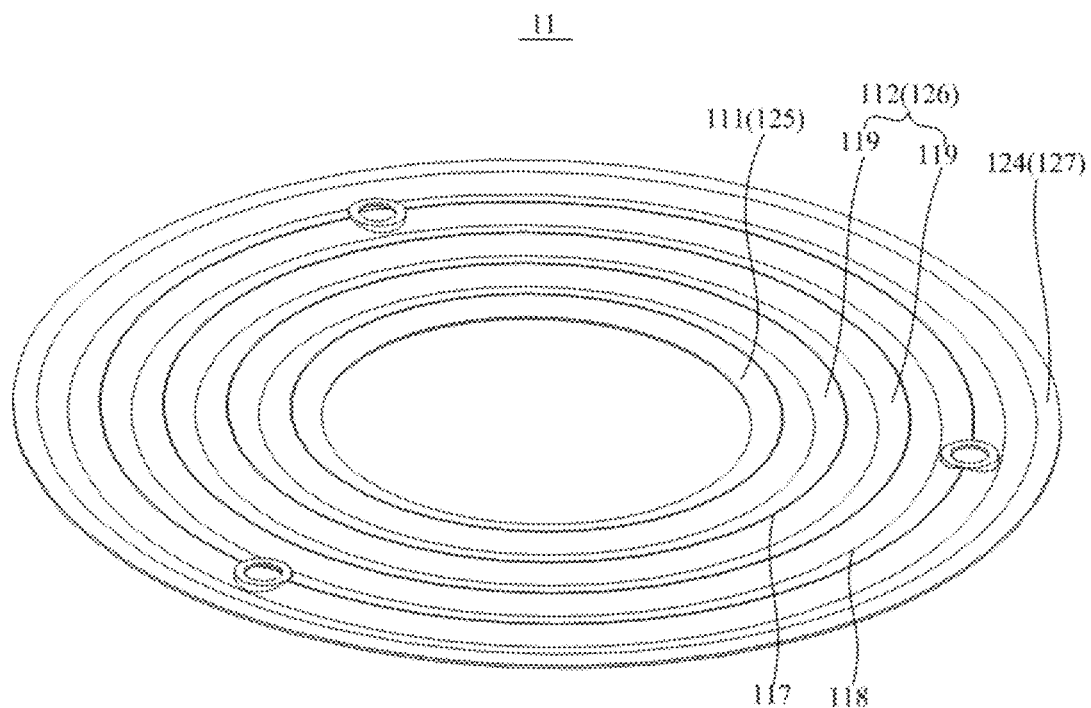
FIG. 20 is a schematic diagram showing the structure of light cap in FIG. 19.
Figure 21:
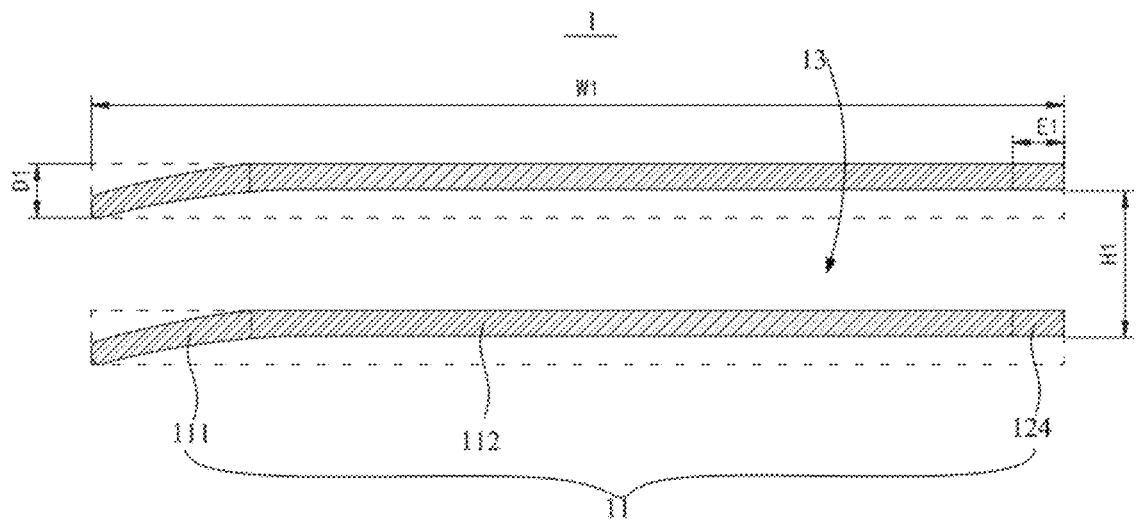
FIG. 21 is a schematic diagram showing dimensional data of the horizontal grating scheme A.
Figure 22:
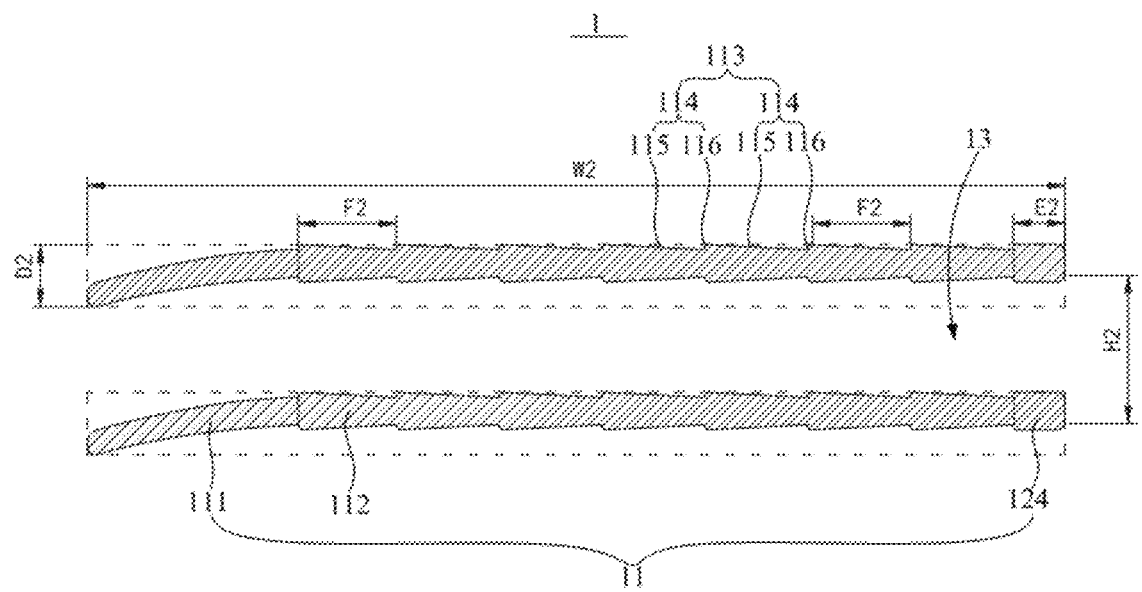
FIG. 22 is a schematic diagram showing dimensional data of stepwise grating scheme B.
Figure 23:
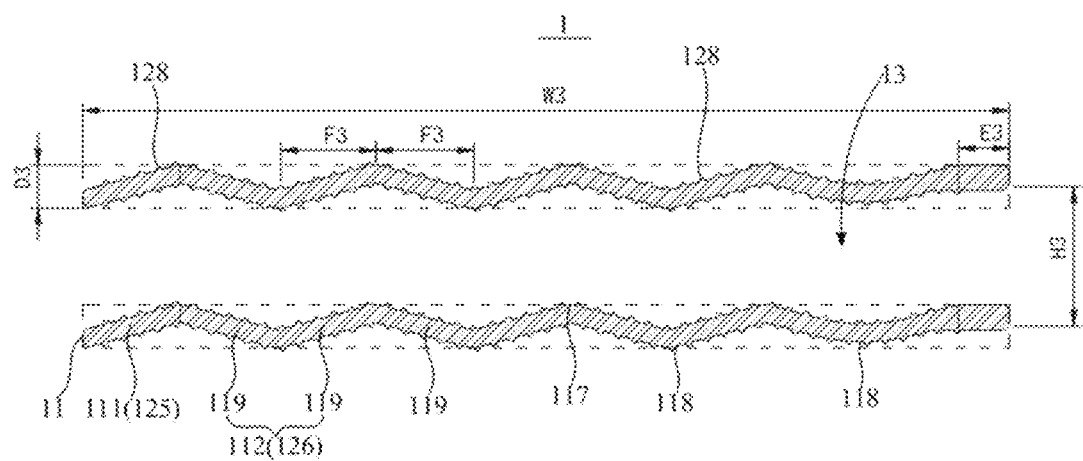
FIG. 23 is a schematic diagram showing dimensional data of the waveform grating scheme D1.
Figure 24:
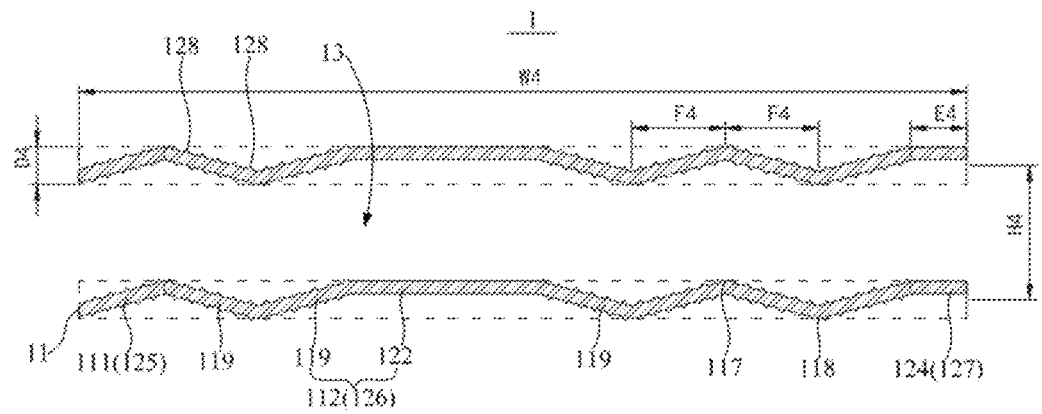
FIG. 24 is a schematic diagram showing dimensional data of the waveform grating scheme D2.
Figure 25:
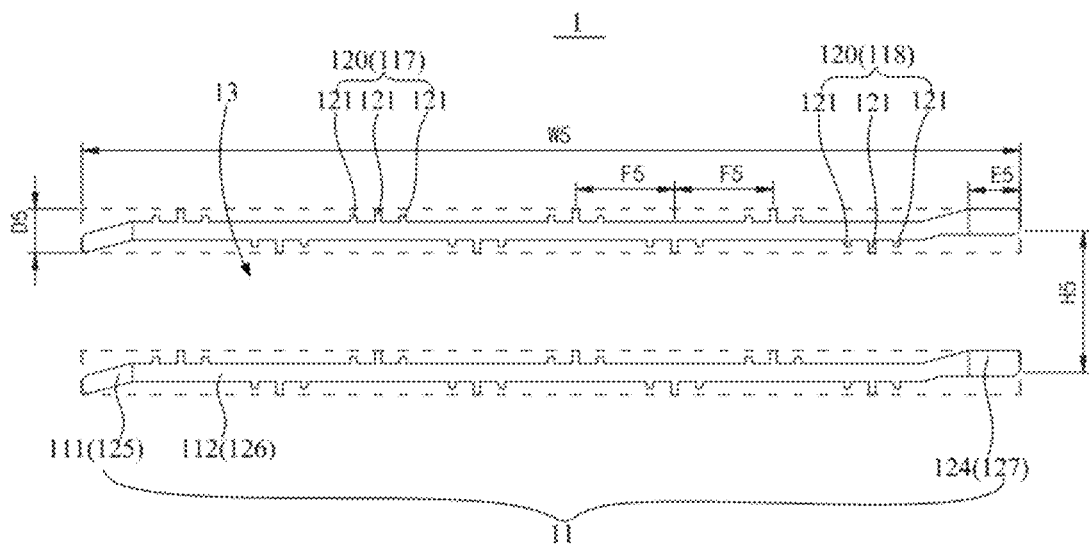
FIG. 25 is a schematic diagram showing dimensional data of the waveform grating scheme D3.

In one embodiment (FIG. 18), the baffle 11 is provided in a strip shape, and the light emission direction of the light outlet 13 is the width direction of the baffle 11. In such a case, the shape of the baffle 11 is relatively simple, which can improve the convenience of processing. Of course, the present invention is not limited to this. In other embodiments (FIG. 19 and FIG. 20), the baffle 11 is provided in a circle, and the incoming light section 111 of the baffle 11 is on the inner side of the baffle 11. In such a case, the baffle 11 can be a circle, square or other circular structures. The UV light source 2 is provided on the inner side of the circular structure. In addition, the baffles 11 can be provided oppositely in the up-down direction (in other words, the connecting line of outgoing light section 124 of multiple baffles 11 is a vertical line), or can be slightly staggered (in other words, the connecting line of outgoing light section 124 of multiple baffles 11 is an inclined line that forms an included angle with the up-down direction).

VI. As shown in FIG. 21-FIG. 25, the data about the grating structure 1 of scheme A, scheme B, scheme C and scheme D are as shown in the following table:

| Grating scheme | Width W of baffle | | Effective thickness D of baffle | | Clearance H of baffles | | Length E of the outgoing light section | | The length of the long side of the step/horizontal distance F between the upper convex and the lower convex | |
|---|---|---|---|---|---|---|---|---|---|---|
| Scheme A | W1 | 57 | D1 | 3.17 | H1 | 8.6 | E1 | 3 | F1 | / |
| Scheme B | W2 | 57 | D2 | 3.63 | H2 | 8.6 | E2 | 3 | F2 | 5.72 |
| Scheme C | / | / | / | / | / | / | / | / | / | / |
| Scheme D1 | W3 | 57 | D3 | 2.66 | H3 | 8.6 | E3 | 3.13 | F3 | 6 |
| Scheme D2 | W4 | 57 | D4 | 2.43 | H4 | 8.6 | E4 | 3.6 | F4 | 6 |
| Scheme D3 | W5 | 57 | D5 | 2.68 | H5 | 8.6 | E5 | 3.13 | F5 | 6 |

Notes:
(1) Unit: mm;
(2) The clearance of baffles is the distance between center points of baffles (FIG. 21-FIG. 25);
(3) D2 and D3 are the extension of the embodiment of scheme D1;
(4) Data of the scheme B are the same as that of the scheme C;

According to the data in the above table, the width of baffles in scheme A, scheme B, scheme C and scheme D remains the same, the clearance H of two adjacent baffles 11 remains the same too, and the effective thickness D of baffles in scheme D is also smaller than that in scheme A, scheme B and scheme C. It is shown that main technical characteristics of decreasing the luminous angle of the grating structure 1 lies in that the second plate body 126 of the baffle 11 is provided with the upper convexes 117 and the lower convexes 118, instead of increasing the width of the baffle 11 and the height of the baffle 11 or shortening the clearance between adjacent baffles 11. When decreasing the thickness of baffles 11 but not increasing the width of baffles 11, the luminous angle is decreased. In scheme A, to decrease the luminous angle, the width of baffles 11 can be expanded to 100 mm, while the width of baffles 11 in scheme D is only 57 mm, significantly decreasing the volume of the grating structure 1 and the UV light 100.

Figure 6:
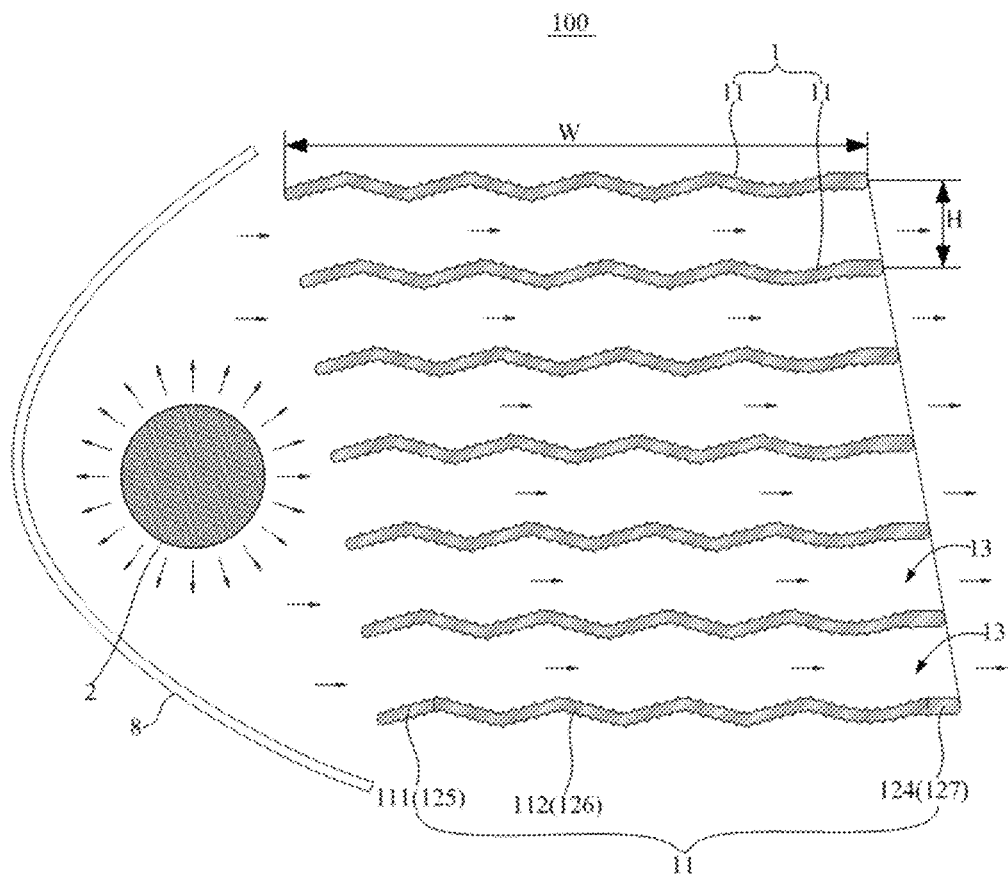
FIG. 6 is a schematic diagram showing the cross section of the UV light in the outgoing light direction in waveform grating scheme D1.

As shown in FIG. 6, the present invention also provides a UV light 100 comprising the grating structure 1 whose specific structure is as shown in the above embodiment. Since the UV light 100 adopts all the technical schemes of all the above-mentioned embodiments, at least the UV light 100 possesses all the beneficial effects brought by the above-mentioned embodiments, such beneficial effects are not described in details here. The UV light 100 can comprise the UV light source 2 provided on one side of the incoming light section 111 of the baffle 11 of the grating structure 1. Further, the UV ray module can also comprise a reflective housing 8 provided on one side of the UV ray module deviating from the grating structure 1 to adjust the luminous angle of UV rays to make UV rays be emitted by facing the grating structure 1.

The above description only presents the preferred embodiments of the present invention, and it is not for this reason that the patent scope of the invention is limited. Any equivalent structural transformation made by using the description of the invention and the drawings, or direct/indirect application in other related technical fields under the inventive concept of the invention, is included in the patent protection scope of the invention.

What is claimed is:

1. A grating structure comprising:
    baffles provided at intervals, wherein an upper surface and a lower surface of each baffle further comprise a light absorption layer, adjacent baffles enclose each other to form a light outlet in a light emission direction of the light outlet, each baffle further comprises a first plate body, a second plate body and a third plate body connected in sequence, the second plate body is configured as a light filter, has a convex upper surface and a convex lower surface, and a height difference between the convex upper surface and the convex lower surface is greater than 1.5 mm.

2. The grating structure of claim 1, wherein the second plate body has a curved shape configured to form continuous waveforms from the convex upper surface and the convex lower surface.

3. The grating structure of claim 2, wherein the convex upper surface and the convex lower surface of the second plate body are connected in sequence to form the continuous waveform, and the second plate body is connected to a horizontal plate body.

4. The grating structure of claim 2, wherein the convex upper surface and the convex lower surface of the second plate body are connected in sequence to form the continuous waveform.

5. The grating structure of claim 2, wherein both the upper surface of the second plate body and the lower surface of the second plate body are planar.

6. The grating structure of claim 2, wherein both the upper surface of the second plate body and the lower surface of the second plate body are curved.

7. The grating structure of claim 2, wherein one surface of the second plate body is curved while a different surface of the second plate body is planar.

8. The grating structure of claim 1, wherein, when multiple baffles are stacked, the upper surface of a lower baffle is contiguous to a lower surface of an upper baffle.

9. The grating structure of claim 1, wherein both the upper surface and the lower surface of each baffle are vertical relative to the light emission direction.

10. The grating structure of claim 1, wherein each baffle has an elongated rectangular shape, and the light emission direction of the light outlet corresponds to a shorter dimension of the elongated rectangular shape.

11. The grating structure of claim 1, wherein the second plate body has a slab shape that comprises multiple convex rib groups.

12. The grating structure of claim 1, wherein each baffle is made of an aluminum alloy, each baffle is treated with anodic oxidation, and the light absorption layer is formed after the anodic oxidation.

13. The grating structure of claim 1, wherein the first plate body is configured as an incoming light section and has a curved shape.

14. The grating structure of claim 1, wherein the third plate body is configured as an outgoing light section and has a horizontal extension.

15. The grating structure of claim 1, wherein each baffle has a circular shape and the first plate body, configured as an incoming light section, is located inside the circular shape.

16. An ultraviolet (UV) light comprising:
a grating structure comprising baffles provided at intervals, wherein an upper surface and a lower surface of each baffle further comprise a light absorption layer, adjacent baffles enclose each other to form a light outlet in a light emission direction of the light outlet, each baffle further comprises a first plate body, a second plate body and a third plate body connected in sequence, the second plate body is configured as a light filter, has a convex upper surface and a convex lower surface, and a height difference between the convex upper surface and the convex lower surface is greater than 1.5 mm.

17. The UV light of claim 16, further comprising:
multiple connecting cylinders, wherein each cylinder of the multiple connecting cylinders is connected to an adjacent cylinder;
central columns; and
nuts, wherein
a lower surface of a lowest baffle among the baffles is contiguous to one end of a particular cylinder of the multiple connecting cylinders, mounting holes that correspond to respective cylinders of the multiple connecting cylinders are configured to set positions of other baffles, the central columns pass through the mounting holes, a lateral peripheral surface of a lower end of the central columns is provided with a convex mounting part that is contiguous to a lower surface of a lowest cylinder of the multiple connecting cylinders, and the nuts connect to an upper end of the central columns and are contiguous to an upper surface of a highest baffle among the baffles, and the nuts and the central columns are configured to clamp and fix the baffles and the multiple connecting cylinders.

18. The UV light as claimed in claim 17, further comprising:
a housing; and screws, wherein an inner bottom wall of the housing connects to two bending plates that enclose the inner bottom wall of the housing to form a chute, the grating structure is provided inside the housing, the convex mounting part is installed in the chute via one end of the two bending plates, an upper surface of the convex mounting part is contiguous to a top wall of the chute, and the screws pass through a top wall of the housing and connect to the central columns to fix the grating structure into the housing.

* * * * *